US006987191B1

(12) United States Patent
Bertola et al.

(10) Patent No.: US 6,987,191 B1
(45) Date of Patent: Jan. 17, 2006

(54) PROCESS FOR THE PRODUCTION OF N-METHYL PYRROLIDONE USING GAMMA BUTYROLACTONE AND MIXED METHYLAMINES AS STARTING MATERIALS

(75) Inventors: Aldo Bertola, Milan (IT); Salvatore Cassarino, Rome (IT); Philippe Raucq, Lustin (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 153 days.

(21) Appl. No.: 10/111,452

(22) PCT Filed: Oct. 25, 2000
(Under 37 CFR 1.47)

(86) PCT No.: PCT/EP00/10509

§ 371 (c)(1),
(2), (4) Date: Feb. 10, 2003

(87) PCT Pub. No.: WO01/30755

PCT Pub. Date: May 3, 2001

(30) Foreign Application Priority Data

Oct. 27, 1999 (BE) .................................... 9900702

(51) Int. Cl.
*C07D 207/267* (2006.01)

(52) U.S. Cl. .................................................. 548/552

(58) Field of Classification Search ................. 548/552
See application file for complete search history.

(56) References Cited

U.S. PATENT DOCUMENTS

| 6,008,375 A | 12/1999 | Bergfeld et al. |
| 6,248,902 B1 | 6/2001 | Bertola |

FOREIGN PATENT DOCUMENTS

| DE | 2 159 859 | 7/1972 |
| DE | 42 03 527 | 8/1993 |
| JP | 47-018751 | * 5/1972 |
| JP | 1 190667 | 7/1989 |
| JP | 09057100 | 3/1997 |
| WO | 99/52867 | 10/1999 |

OTHER PUBLICATIONS

XP-002161172, Chem. Abstr. Jan. 21, 1989.
XP-002161171, Chem. Abstr. May 30, 1972.
Chemical Abstracts vol. 124, No. 11, p. 1230 XP-002113414, Nov. 3, 1996.
Chemical Abstracts vol. 43, No. 11 XP-002113415, Oct. 6, 1949.
Chemical Abstracts vol. 31, No. 7 XP-002113416, Oct. 6, 1937.
Ullmann's Encyclopedia of Industrial Chemistry, Fifth, Completely Revised Edition, vol. A22, pp. 457-461 1993.

* cited by examiner

*Primary Examiner*—Taofiq Solola
*Assistant Examiner*—Ebenezer Sackey
(74) *Attorney, Agent, or Firm*—Oblon, Spivak, McClelland, Maier & Neustadt, P.C.

(57) ABSTRACT

A process for the production of N-methyl pyrrolidone using gamma butyrolactone and mixed methylamines as starting materials, in a continuous process, in such operating conditions as to allow the production of high purity N-methyl pyrrolidone in high yields.

13 Claims, 2 Drawing Sheets

Figure 1:
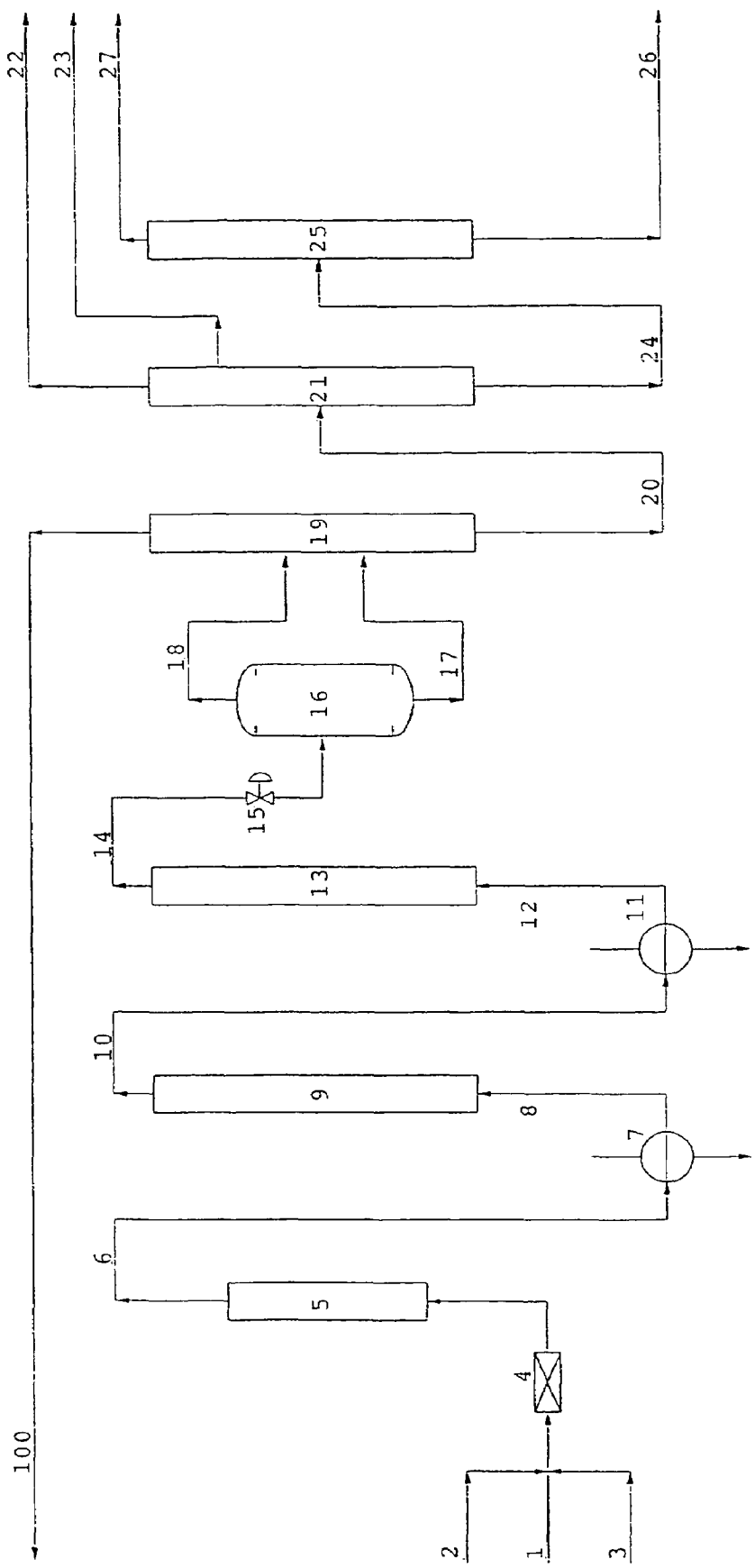

PROCESS FOR THE PRODUCTION OF N-METHYL PYRROLIDONE USING GAMMA BUTYROLACTONE AND MIXED METHYLAMINES AS STARTING MATERIALS

BACKGROUND

The present invention relates to the production of N-methyl pyrrolidone (NMP). In particular, it relates to the use of gamma-butyrolactone (GBL) and mixed methylamines as starting materials, in such a way that the product is obtained by a continuous process in optimal purity and yields.

It is known from the prior art that there exist several processes for the synthesis of N-methyl pyrrolidone, using GBL and one methylamine, monomethylamine (MMA), as starting materials.

In J. Am. Chem. Soc., March 1949, pag. 897, Elvain and Vozza described a synthetic strategy aimed at the production of NMP with GBL and MMA as starting materials that exploited a discontinuous process, and with a double amount of the latter in comparison with his stoichiometric value.

After 4 hours of reaction at 280° C., NMP was recovered by distillation with a 90–93% yield.

In 1936 Spath and Lunder (Berichte 69, pag. 2727) described a similar process wherein a large excess of methylamine (4 mols per mol of GBL) was fed to a discontinuous reactor, with an approximately 90% conversion after 3 hours.

JP-A-72/018751 discloses a discontinuous process for the preparation of NMP by heating GBL with DMA and TMA. The reaction temperature is 230–300° C. The reaction time is in the range of about 0 to 5 hours. After terminating the reaction, the separation of NMP can be performed by subjecting the reaction mixture to fractional distillation.

NMP product purification involved complex dissolution processes, to be carried out in the ether from the effluent of the reaction and the ensuing distillations. In several patents (JD 7 221 420; JP 740025,G; JP 7 420 585; JP 7 642 107) Mitsubishi Chemical Industries Co. Ltd. of Japan described continuous processes for the synthesis of NMP using GBL and MMA as starting materials. These are characterised by reactions with high molar ratios between water and GBL (typically ranging between 3 and 4 mols of water for each mol of GBL) and by the presence of great amounts of MMA (typically with molar ratios ranging between 1.4 and 3 mols of MMA per mol of GBL).

JP-A-01/190 667 teaches the preparation of NMP at 240–265° C. by reacting GBL with MMA, isolating the by-products DMA and TMA from the obtained reaction mixture and recirculating these by-products into the reaction system.

The processes designed by Mitsubishi result to be disadvantageous in terms of the high costs involved with the separation of unreacted MMA and its recovery and with the separation of the water forwarded to the reaction to which synthesis water adds up (one mol of water for each mol of reacted GBL).

To avoid the drawbacks associated with the discontinuous reaction in the presence of excess MMA and water, alternative methodologies have been proposed and these are based on the employment of catalysts. In German Patent No. 2,159,858 owned by Mobil Oil a synthesis with GBL, MMA in the presence of 13X type zeolites is described.

The above processes did not succeed in being applied industrially, as the employment of a catalyst subject to regenerations is disadvantageous in terms of the economic balance of the process as compared with non catalytic processes.

In WO-A-99/52867 the same Applicant discloses a process for the production of N-Methyl Pyrrolidone by reacting in a continuous mode a light excess of pure monomethylamine with gamma-butyrolactone under pressure and without catalyst by using a three stage reactor connected in series.

The present application is an improved low cost process to afford N-Methyl Pyrolidone by reacting gamma-butyrolactone with a mixture of methylamines.

The advantage of this application is the direct link established between a N-Methyl Pyrrolidone plant and a Methylamines plant for a cheaper design. It is known that reacting ammonia and methyl over an amination catalyst produces a mixture of mono-, di- and trimethylamines. The separation of this mixture involves a complex separation sequence which increases significantly the price of pure methyl amines.

So, it is a first advantage of the present application to offer a process in which a low cost mixture of methylamines (coming directly from the ammonia-methanol reaction without a costly fractional distillation step) is used to produce N-Methyl Pyrrolidone.

There is a second advantage of the present application. It is known in the prior art that reacting separately gammabutyrolactone with mono-, di- and trimethylamines produces N-Methyl Pyrrolidone with water and, for the two last amines, water and methanol.

According to the present invention, by using the process disclosed in WO-A-99/52867, the use of a mixture of methylamines allows the production of N-Methyl Pyrrolidone, in absence of added water, still in high purity and yield. The unreacted di and trimethylamines (and methanol) are recycled in the amination section.

The above feature gives way to the production of NMP at low investment costs, using cheaper raw materiali and inferior utility consumptions, compared with the technologies of the previous art.

DESCRIPTION OF THE INVENTION

As known in the art, ammonia and methanol, reacting over an animator catalyst, produce a mixture of mono, di and trimethylamines (MMA, DMA, TMA).

The separation or the methylamines involves a complex sequence of 4 to 5 fractionators requiring significant investment and high energy consumptions.

The design of a methylamine plant can be driven toward the production of one methylamine only by recycling to the amination reactor the remaining unwanted methylamines.

This practice, however, requires additional investments and more heavy energy consumptions. Due to the above contraints a producer of NMP using GBL and MMA as feedstocks would produce MMA only in case he can economically dispose the coproducts DMA and TMA.

The major innovation of the process of this invention is the possibility of using mixtures of methylamines in place of MMA in the production of NMP, making possible to establish a direct link between a NMP plant and a methylamines plant of cheaper design.

The synthesis of NMP from GBL and mixed amines follows basically the same principles of the synthesis from GBL and MMA.

While one mole of GBL reacting with one mole of MMA forms one mole of NMP and one mole of water, the reaction of one mole of GBL with one mole of DMA or with one mole of TMA forms, besides one mole of NMP, respectively one or two moles of methanol.

Consequently the product of the reaction will contain, besides NMP, non converted amines, water, methanol plus light and heavy by products.

Methanol and non converted amines, separated from the effluent of reaction, will be recycled to the amination reactor where, in presence of ammonia and of additional methanol, will be converted into mixed methylamines.

The production of NMP from GBL and mixed methylamines in the process of this invention is characterized in that the synthesis is carried out by a continuous non catalytic process in the liquid phase, via distinct reaction stages, preferably, but not limited to, three connected in series.

According to the present invention three stages of the reaction leading to the production of NMP are characterised by what follows:

| I stage of reaction | | |
|---|---|---|
| Amines: GBL molar ratio | = | between 1.05 and 1.5 |
| Temperature (reactor outlet) | = | between 150 and 220° C. |
| Residence time | = | between 10 and 40 minutes |
| II stage of reaction | | |
| Temperature | = | between 220 and 270° C. |
| Residence time | = | between 1 and 3 hours |
| III stage of reaction | | |
| Temperature | = | between 250 and 310° C. |
| Residence time | = | between 0.5 and 2.0 hours |

In the three reactors the pressure ranges between 40 and $100.10^5$ Pa, so as to keep the reactants in their liquid phase.

All reactors are of the adiabatic type and preferably tubular in shape.

Adequate reactors are also vessels subdivided into compartments by means of separation septs that avoid the reaction products to mix again as the reaction progresses.

In the first reactor GBL exothermally reacts with the amines to afford Production of hydroxybutyramide (NMH). In the following reactor NMH cyclisation reaction is triggered with formation of water, methanol and NMP.

In the final stage, the NMP formation reaction goes to completion at high temperature.

The succession of the subsequent reaction stages as they are described in the present process leads to a reduction in GBL and NMH contents in the reaction effluents, which is a necessary condition for producing high purity NMP (99.5% minimum weight).

GBL, whose boiling point is very close to that of MMP (202° C.) would not be separated from NMP by distillation.

During distillation, NMH would tend to go off again yielding MMA and GBL that would contaminate the product because not separable.

DESCRIPTION OF THE PROCESS

The features of the process of this invention will be more readily apparent from the following description of the preferred embodiments of the invention with reference to the accompanying drawings in which the process schemes are shown. In the drawings FIG. 1 shows a schematic representation of a process object of this invention for producing NMP from GBL and mixed methylamines.

Figure 2:
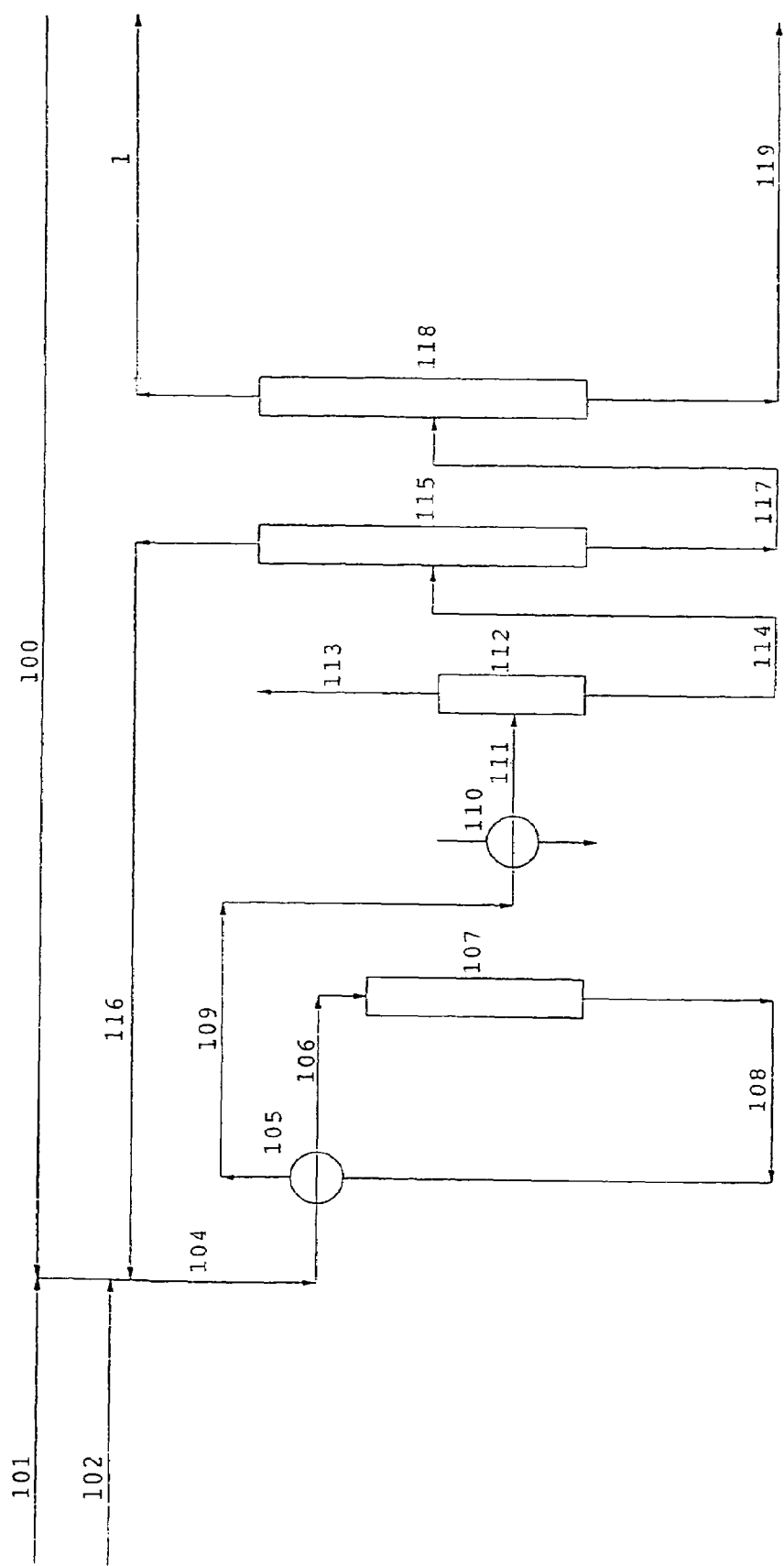

FIG. 2 shows a schematic representation of a process for producing mixed methylamines integrated with the NMP process object of this invention.

With reference to FIG. 1, mixed amines (line 1) mix with water (line 2) and with GBL (line 3) in static mixer 4 with a molar ratio of about 1.2:1 between methylamines and GBL.

The mixing activates the addition reaction with formation of NMH.

This reaction is exothermal and once gone to completion takes the mass temperature up to about 190° C.

The addition reactions go to completion in reactor 5 within about 20 minutes.

The liquid stream from the reactor (line 6) is heated up further in exchanger 7, by means of hot oil, and its temperature is taken up to 250° C.

After preheating, the liquid (line 8) feeds reactors 9 where NMH starts to cyclise, while water and methanol are formed at the same time.

Residence time in reactor 9 is approximately 2 hrs. The reactor is of the tubular type, otherwise it is a vessel subdivided into compartments by separation septs that have the function of keeping the reaction products from mixing again.

The effluents from reactor 9 (line 10) feed heater 11 where temperature is raised to 280° C. by thermal exchange with hot oil.

After the second preheating, the liquid (line 12) feeds reactor 13 where conversion of NMH to NMP goes to completion with an approx. 1.5 hr. of residence time. Through valve 15, the effluent pressure is reduced producing a liquid phase in separator 16 (line 17), and a vapour phase (line 18) which both feed fractionation column 19 where non converted methylamines and methanol separate overheads and are recycled to the amination reactor in the methylamine plant (line 100).

The bottom product of column 19 feeds (line 20) subsequent column 21, wherein at the top reaction water separates (line 22) while light organic byproducts are obtained too (line 23).

The bottom product in column 21 feeds (line 24) fractionation column 25 where at the bottom heavy by-products are disposed (line 26) whereas at the top (line 27) purified NMP separates.

After GC analysis NMP results to be no less pure than 99.5% by weight, with a water content lower than 0.05% by weight.

FIG. 2 shows a schematic representation of a process for producing mixed methylamines integrated with the NMP process object of this invention.

Non converted amines and methanol stream from the NMP plant (line 100) join make up ammonia (line 101), make up methanol (line 102) and a recycling ammonia rich stream (line 116).

The mixture (line 104) after preheating (105) flows (line 106) to the amination reactor 107.

The reactor effluent (line 108) preheats the reactor feed in 105 and, following the preheater, (line 109) is condensed in cooler 110.

The condensate flows (line 111) to separator 112, where gases containing carbon monoxide and hydrogen are separated (line 113). The condensate flows (line 114) to column 115 which separates overheads (line 116) an ammonia-trimethylamine stream, which is recycled (line 116). Bottoms of column 115 flow (line 117) to column 118 which separates at bottoms water to be disposed (line 119) and overheads a stream of mixed methylamines which flows to the NMP plant (line 1).

What is claimed is:

1. A process for the production of N-methyl-pyrrolidone, which comprises:
    reacting gamma butyrolactone and mixed methylamines consisting of a mixture of mono, di and trimethylamine or any combination of the abovementioned methylamines
    wherein the reacting occurs in a continuous non catalytic manner in the liquid phase, via stages of reaction connected in series; and
    recycling effluent obtained from said reacting to an amination reactor;
    wherein said effluent comprises unreacted mixed methylamines and methanol; and then
    contacting the effluent comprising unreacted mixed methylamines and methanol with ammonia and with externally added methanol to obtain a mixture comprising mixed methylamines.

2. A process according to claim 1, wherein there are three stages of the reaction having the following characteristics:
    a) the first stage of the reaction operates at a temperature ranging between 150° C. and 220° C. at the reactor outlet, with a residence time ranging between 10 and 40 minutes;
    b) the second stage of the reaction operates at a temperature ranging between 220° C. and 270° C. at the reactor inlet, with a residence time ranging between 1 and 3 hrs;
    c) the third stage of the reaction operates at a temperature ranging between 250° C. and 310° C. at the reactor inlet, with a residence time ranging between 0.5 and 2 hrs.

3. A process according to claim 1, wherein a first stage of the reaction operates at a temperature ranging between 170° C. and 200° C. at the reactor outlet.

4. A process according to claim 1, wherein a first stage of the reaction has a residence time that ranges from 15 to 25 minutes.

5. A process according to claim 1, wherein a second stage of the reaction has a residence time that ranges from 1.5 to 2.5 hrs.

6. A process according to claim 1, wherein a third stage of the reaction has a residence time that ranges from 1.0 to 1.5 hours.

7. A process according to claim 1, wherein said reacting the molar ratio between mixed methylamines and gammabutyrolactone ranges from 1.05 to 1.5.

8. A process according to claim 1, wherein said reacting the molar ratio between mixed methylamines and gammabutyrolactone ranges from 1.1 to 1.3.

9. A process according to claim 1, wherein said reacting the reactants are kept in the liquid phase by operating the reaction system at pressure that ranges from 40 to 100 ATE.

10. A process according to claim 1, wherein said reacting occurs at pressure that ranges from 60 to 80 ATE.

11. A process according to claim 1, wherein reactors of each of the reaction stages consist of vessels having septs with the function of creating a piston-reactant-flow through separate reaction compartments which keep the products from remixing.

12. A process according to claim 11 wherein the reactors of each of the reaction stages consist of vessels characterized by being tubular.

13. A process for the production of N-methyl-pyrrolidone according to claim 1, wherein said recycling is integrated with said reacting.

* * * * *